United States Patent [19]

Suzuki et al.

[11] Patent Number: 5,246,432
[45] Date of Patent: * Sep. 21, 1993

[54] DISPOSABLE ABSORBENT ARTICLES

[75] Inventors: Migaku Suzuki, Kamakura; Satoshi Nozaki, Ehime; Takeshi Kudo, Kawanoe; Kazuaki Ohnishi, Kakegawa; Shigeo Imai, Iyomishima, all of Japan

[73] Assignee: Uni-Charm Corporation, Ehime, Japan

[*] Notice: The portion of the term of this patent subsequent to Oct. 29, 2008 has been disclaimed.

[21] Appl. No.: 777,077

[22] Filed: Oct. 16, 1991

Related U.S. Application Data

[63] Continuation of Ser. No. 551,904, Jul. 12, 1990.

[51] Int. Cl.⁵ .............................................. A61F 13/15
[52] U.S. Cl. .................. 604/385.2; 604/378; 604/385.1
[58] Field of Search ............... 604/358, 385.1, 385.2, 604/389, 378

[56] References Cited

U.S. PATENT DOCUMENTS

| 4,704,116 | 11/1987 | Enloe . | |
| 4,892,528 | 1/1990 | Suzuki . | |
| 5,061,261 | 10/1991 | Suzuki et al. | 604/385.2 |
| 5,167,653 | 12/1992 | Igaue et al. | 604/385.2 |
| 5,188,627 | 2/1993 | Igaue et al. | 604/385.2 |

FOREIGN PATENT DOCUMENTS

| 0243013 | 10/1987 | European Pat. Off. . |
| 2181336 | 4/1987 | United Kingdom . |
| 2193625 | 2/1988 | United Kingdom . |
| 2212382 | 7/1989 | United Kingdom . |

Primary Examiner—Randall L. Green
Assistant Examiner—R. Clarke
Attorney, Agent, or Firm—Lowe, Price, LeBlanc and Becker

[57] ABSTRACT

A disposable absorbent article having a topsheet, a backsheet, an absorbent core, first flaps and second flaps. Each of second flaps is connected to the first flap and has a section branching upward and a section extending outward. The branching section is partially elastic. The extending section is so constructed as to be liquid-absorbent on its top surface.

4 Claims, 2 Drawing Sheets

DISPOSABLE ABSORBENT ARTICLES

This is a continuation of application Ser. No. 07/551,904, filed Jul. 12, 1990 and the benefits of 35 USC 120 are claimed relative to it.

BACKGROUND OF THE INVENTION

The present invention relates to disposable absorbent articles and, more particularly, to such articles, for example, disposable diapers comprising a liquid-permeable topsheet, a liquid-impermeable backsheet, an absorbent core sandwiched between the top- and backsheets, first flaps outwardly extending from opposite side edges of the absorbent core, respectively, and second flaps connected to the associated first flaps, each of said second flaps comprising a section branching upward from top surface of the associated first flap and being partially elastic so as to serve as a liquid barrier, on one hand, and a section extending outward from the branching line, on the other hand.

It has already been proposed, for example, by Japanese Patent Application Disclosure Gazettes Nos. 1984-25741 and 1987-25020 to provide an absorbent article not only with elastic flaps extending outward from opposite side edges thereof but also with additional flaps rising from the top surface of the absorbent article at the locations inside said opposite side edges, said additional flaps serving as liquid barriers and being partially elastic, so that these additional flaps may substantially prevent any quantity of urine from flowing out of the absorbent article, confining the quantity of urine inside these flaps.

Such arrangement is certainly effective for prevention of urinary leakage but disadvantageous in that the quantity of urine confined in a space between the additional flaps and gathers of the outer extending elastic flaps often causes skin diseases such as eczema and eruption because no liquid absorbing component is present in said space and the wearer's skin is kept contact with said quantity of urine confined therein.

It is an object of the invention to provide disposable absorbent article having flaps branching upward and partially elastic so as to serve as liquid barriers, said flaps being povided on the top surface of the sections horizontally extending outward from the respective branching lines with liquid absorbency and thereby to eliminate the above-mentioned inconvenience.

SUMMARY OF THE INVENTION

The object set forth above is achieved, in accordance with the present invention, by disposable absorbent article comprising a liquid-permeable topsheet, a liquid-impermeable backsheet, an absorbent core sandwiched between the top- and backsheets, first flaps outwardly extending from opposite side edges of the absorbent core, respectively, and second flaps connected to the associated first flaps, each of said second flaps comprising a section branching upward from the top surface of the associated first flap and being partially elastic so as to serve as a liquid barrier, on one hand, and a section horizontally extending outward from the branching line, on the other hand, characterized in that said section of each second flap horizontally extending outward from the branching line is provided on its top surface with liquid absorbency.

PREFERRED EMBODIMENT OF THE INVENTION

The present invention will be described by way of example, as embodiment in disposable diaper, in reference with the accompanying drawings.

Figure 1:
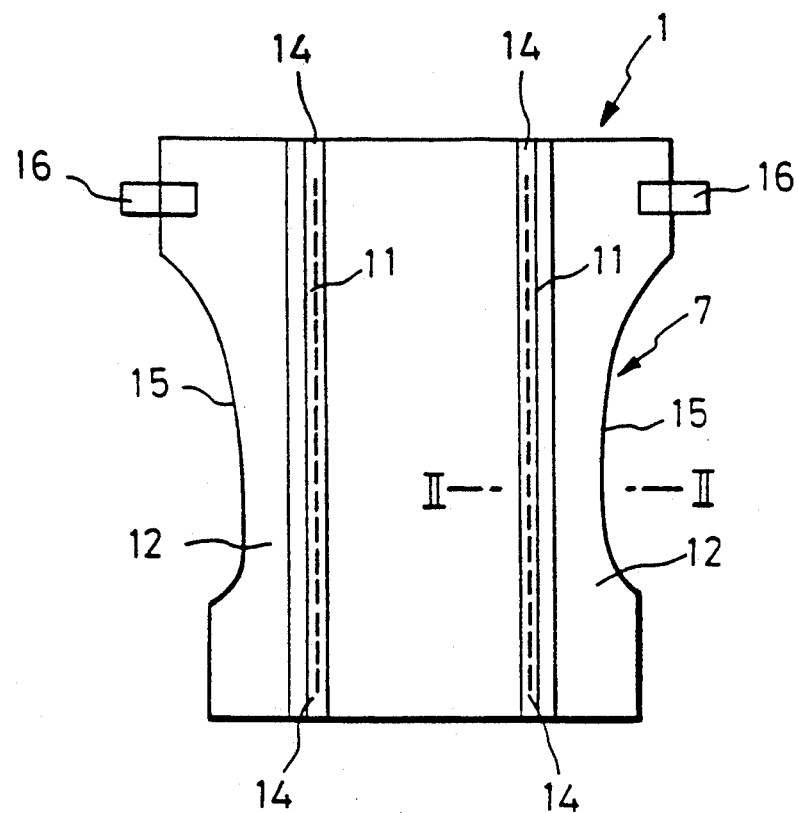
FIG. 1 is an unfolded plan view of diaper as an example of the article constructed according to the present invention.
Figure 2:
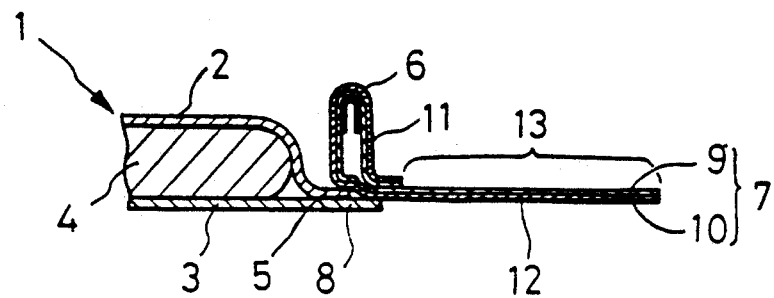
FIG. 2 is a sectional view taken along a line II—II in FIG. 1.

Referring to FIGS. 1 and 2, diaper 1 comprises a liquid-permeable topsheet 2 adapted to be in contact with the wearer's skin when it is put on, a liquid-impermeable backsheet 3 adapted to be not in contact with the wearer's skin, a liquid absorbent core 4 sandwiched between these two sheets 2, 3, first flaps 5 extending outward from respective side edges of said core, and second flaps 7 connected to outer edges 8 of the respective first flaps and having elastic members 6.

Each of the second flaps 7 is a combined sheet of a liquid absorbent sheet 9 and a liquid-impermeable and moisture-permeable sheet 10 so that such combined sheet totally serves as a liquid barrier. One end of the second flap 7 is folded back to form a sleeve 11 and the remainder of the flap 7, i.e., a section defined by the sleeve 11 extends outward from the sleeve 11, a section 13 thereof having liquid absorbency on its top surface. An elastic member 6 doubled into a cross-section of inverted U-shape is mounted within the sleeve 11 so as to be elastic longitudinally of the latter and thereby to provide the sleeve 11 with longitudinal elasticity. Specifically, the sleeve 11 is maintained in its upright posture under its contractile force. Longitudinally opposite ends 14 of the sleeve 11 are often collapsed inward and bonded onto the associated first flap. It is also possible that said opposite ends are collapsed outward and bonded onto the outer section 13 of the second flap or that the one end 14 is collapsed inward and bonded onto the first flap while the other end 14 is collapsed outward and bonded onto the outer section 13 of the second flap.

Figure 3:
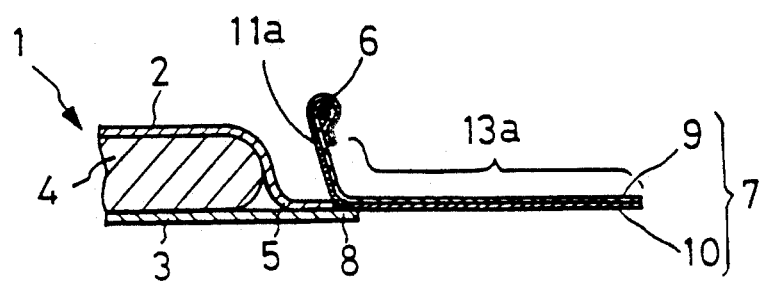
FIG. 3 is a sectional view similar to FIG. 2 illustrating another embodiment.

With an embodiment illustrated in FIG. 3, the second flap 7 comprises one end rolled around the elastic member 6, the upwardly branching section 11a and the section 13a provided on its top surface with liquid absorbency.

Figure 4:
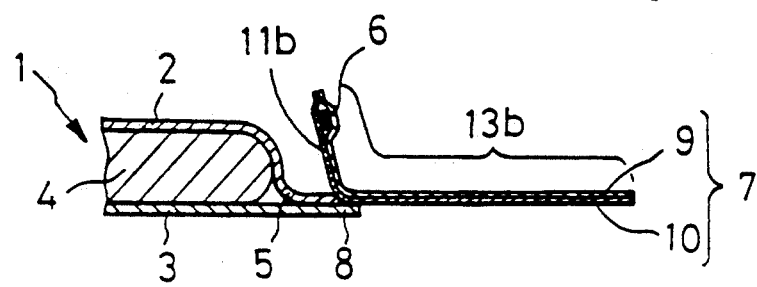
FIG. 4 is a sectional view similar to FIG. 2 illustrating futher another embodiment.

With an embodiment illustrated FIG. 4, the second flap 7 comprises one end sandwiching the elastic member 6 between the both sheets 9, 10, the upwardly branching section 11b and the section 13b having liquid absorbency on its top surface.

Figure 5:
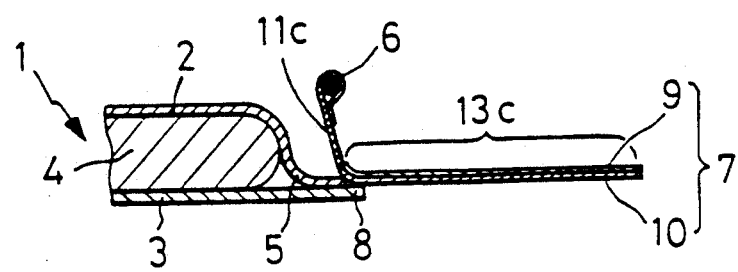
FIG. 5 is a sectional view similar to FIG. 2 illustrating still another embodiment.

With an embodiment illustrated in FIG. 5, the second flap 7 comprises one end and a portion adjacent this end consisting only of the sheet 10, the elastic member 6 around which said one end is rolled, the upwardly branching section 11c and the section 13c having liquid absorbency on its top surface.

Except for the configurations of the respective second flaps, the embodiments illustrated in FIGS. 3 through 5 are identical to the embodiment illustrated in FIG. 2. With the embodiments illustrated in FIGS. 2 through 5, the second flaps 7 are formed along the respective outer edges with curved lines 15, leaving longitudinally opposite ends thereof intact, typically as illustrated in FIG. 1. Furthermore, the second flaps 7 are provided respectively adjacent their upper ends, as viewed in FIG. 1, corresponding to opposite sides of the rear waist with tape fasteners 16, respectively.

Though not shown, there may be also provided elastic members along the curved lines 15 of the respective second flaps 7 and the upwardly branching sections 11, 11a, 11b, 11c of the respective second flaps 7 may be also formed in V-shape.

The topsheet 2 may be made of liquid-permeable nonwoven fabric, porous plastic film or the like, the backsheet 3 may be made of liquid-impermeable plastic film, liquid-impermeable and moisture-permeable plastic film or the like, and the core 4 may be made of fluffy pulp mixed with super absorbent polymer particles, or the like. The sheet 9 may be made of sweat absorbent nonwoven fabric such as spun-bonded fabric, molten-bonded fabric under heat-treatment or molten-blown fabric prepared by extrusion under air-blow, of polyester fibres having hydrophilic surface treatment; cellulose type hydrophilic fibres such as rayon, said fibres having said hydrophilic surface treatment, or the like made entangled under the effect of high pressurized fluid such as water jets with nonwoven fabric of hydrophobic fibres such as polyester, polypropylene or the like; and molten-bonded nonwoven fabric comprising a mixture of fibres having said hydrophilic surface treatment or hydrophilic fibres with said hydrophobic fibres. The fibres having hydrophilic surface treatment or the hydrophilic fibres to be mixed with the hydrophobic fibres preferably occupy 70% or higher of the final nonwoven fabric. The sheet 10 may be made of nonwoven fabric, such as spun-bonded fabric, molten-blown fabric under heat-treatment or molten-blown fabric prepared by extrusion under air-blow, having liquid barrier characteristic and moisutre permeability such as polyester or polypropylene, or micro porous plastic film of polyethylene or the like.

What is claimed is:

1. A disposable liquid absorbing article comprising
   (A) liquid-permeable topsheet (2),
   (B) a liquid-impermeable backsheet (3),
   (C) an absorbent core (4) sandwiched between said top- and backsheets,
   (D) a first set of flaps (5) formed from said topsheet (2) and said backsheet (3) extending laterally outwardly from opposite side edges of the absorbent core (4), and
   (E) a second set of flaps (7) which is formed from material separate from the materials forming said topsheet (2) and said backsheet (3), each of said second flaps (7) being connected to one of each of said first flaps (5), each of said second flaps (7) comprising
      (a) a first section (11) which is formed from material separate from the material forming said topsheet (2) and which extends upwardly from the surface of each first flap (5) and being partially elastic so as to serve as a moisture-permeable liquid barrier, and
      (b) a second section (13) which is also formed from material separate from the material forming said topsheet (2) extending laterally outward from the lower portion of each said first section (11), each second section (13) comprising
         (i) a lower sheet-like layer (10) made of liquid-impermeable and moisture-permeable material, and
         (ii) an upper sheet-like layer (9) that is liquid absorbent and adapted to be in contact with the wearer's skin.

2. An article as recited in claim 1 wherein said upper sheet-like layer (9) is made of nonwoven fabric.

3. An article as recited in claim 1 wherein said liquid-impermeable and moisture-permeable sheet (10) is made of nonwoven fabric or micro porous plastic film.

4. An article as recited in claim 1 wherein said second set of flaps (7) is provided in its upper ends, with an elastic member (6) so that each of said elastic members (6) is covered by a portion of the associated second flap (7).

* * * * *